(12) United States Patent
Ross et al.

(10) Patent No.: US 11,911,099 B2
(45) Date of Patent: Feb. 27, 2024

(54) SYSTEM FOR PERFORMING LASER THERAPY AND METHOD THEREFOR

(71) Applicant: Duke University, Durham, NC (US)

(72) Inventors: Weston Ross, Durham, NC (US); Patrick Codd, Durham, NC (US)

(73) Assignee: Duke University, Durham, NC (US)

( * ) Notice: Subject to any disclaimer, the term of this patent is extended or adjusted under 35 U.S.C. 154(b) by 36 days.

(21) Appl. No.: 16/964,966

(22) PCT Filed: Aug. 20, 2018

(86) PCT No.: PCT/IB2018/056284
§ 371 (c)(1),
(2) Date: Jul. 24, 2020

(87) PCT Pub. No.: WO2019/145763
PCT Pub. Date: Aug. 1, 2019

(65) Prior Publication Data
US 2021/0045810 A1    Feb. 18, 2021

Related U.S. Application Data

(60) Provisional application No. 62/623,159, filed on Jan. 29, 2018, provisional application No. 62/622,452, filed on Jan. 26, 2018.

(51) Int. Cl.
*A61B 18/20* (2006.01)
*G16H 20/40* (2018.01)
(Continued)

(52) U.S. Cl.
CPC ........... *A61B 18/203* (2013.01); *G16H 20/40* (2018.01); *G16H 40/67* (2018.01);
(Continued)

(58) Field of Classification Search
CPC ........ A61B 18/203; A61B 2018/00577; A61B 2018/2015; A61B 2018/2035;
(Continued)

(56) References Cited

U.S. PATENT DOCUMENTS 5,049,147 A    9/1991   Danon
6,706,035 B2   3/2004   Cense et al.
(Continued)

OTHER PUBLICATIONS

Jenny Wang, Christopher Sramek, Yannis M. Paulus, Daniel Lavinsky M.D., Georg Schuele, Dan E. Andersen, David A. Dewey, Daniel V. Palanker, "Retinal safety of near-infrared lasers in cataract surgery," J. Biomed. Opt. 17(9) 095001 (Sep. 14, 2012) https://doi.org/10.1117/1.JBO.17.9.095001 (Year: 2012).*
(Continued)

*Primary Examiner* — Joseph M Dietrich
*Assistant Examiner* — Ranjani Mari Sundaresan
(74) *Attorney, Agent, or Firm* — Kaplan Breyer Schwarz, LLP

(57) ABSTRACT

The present disclosure enables improved laser treatments by enabling better estimation of laser-tissue interaction to better inform the planning of a treatment path for a laser signal through a treatment region. An embodiment in accordance with the present disclosure uses a laser signal to generate a feature in the treatment region, generates a surface profile of the treatment region that includes the feature, compares that surface profile to another surface profile of the treatment region taken before the generation of the feature, and infers at least one property for at least one tissue type in the treatment region based on the comparison. In some embodiments, the feature is generated such that it includes a plurality of tissue types previously identified in the treatment region, thereby enabling inference one or more properties for each tissue type and/or locating one or more boundaries between tissue types.

20 Claims, 6 Drawing Sheets

(51) Int. Cl.
*G16H 40/67* (2018.01)
*A61B 18/00* (2006.01)

(52) U.S. Cl.
CPC ............ *A61B 2018/00577* (2013.01); *A61B 2018/2015* (2013.01); *A61B 2018/2035* (2013.01)

(58) Field of Classification Search
CPC ........ G16H 20/40; G16H 40/67; G16H 30/40; G16H 50/50; G16H 50/20
See application file for complete search history.

(56) References Cited

U.S. PATENT DOCUMENTS

| | | | |
|---|---|---|---|
| 6,984,228 | B2 | 1/2006 | Anderson et al. |
| 8,652,061 | B2 | 2/2014 | Yu et al. |
| 2002/0183811 | A1 | 12/2002 | Irwin |
| 2010/0256965 | A1* | 10/2010 | Rathjen .................. G06F 19/00 703/11 |
| 2011/0319877 | A1* | 12/2011 | Anderson ................ A61B 5/72 606/10 |
| 2012/0059441 | A1 | 3/2012 | Chang et al. |
| 2013/0158530 | A1* | 6/2013 | Goldshleger .......... A61B 3/102 606/6 |
| 2013/0184693 | A1 | 7/2013 | Neev |
| 2016/0158575 | A1 | 6/2016 | Levatter |

OTHER PUBLICATIONS

Authorized Officer: Lee W. Young, International Search Report and Written Opinion issued in counterpart PCT application No. PCT/IB2018/056284, dated Sep. 19, 2019, 15 pp.

* cited by examiner

SYSTEM FOR PERFORMING LASER THERAPY AND METHOD THEREFOR

STATEMENT OF RELATED CASES

This case claims priority to U.S. Provisional Patent Application Ser. No. 62/622,452 filed on Jan. 26, 2018 and U.S. Provisional Patent Application Ser. No. 62/623,159 filed on Jan. 29, 2018, each of which is incorporated herein by reference.

TECHNICAL FIELD

The present disclosure relates to surgical systems in general, and, more particularly, to laser therapies such as laser surgery, tattoo removal, and the like.

BACKGROUND

Laser therapies are widely used for the treatment of many life-threatening conditions, such as brain cancer, skin cancer, and urinary-tract conditions, etc., as well as non-life-threatening ailments, such as cosmetic hair removal, tattoo removal and the like. In a typical laser therapy, a laser signal is directed across the tissue being treated to induce an effect in the tissue, such as ablation or color change.

Unfortunately, the manner in which tissue responds to laser energy depends on many factors, including laser intensity, spot size, health of the tissue, distance between the laser source and the tissue being treated, and more. Tissue response can vary widely, therefore, making it difficult to predict the outcome of a laser-tissue interaction and leading to uncertainty regarding how much optical energy to employ, where to direct the light, how long to keep the laser signal in one spot, etc. As a result, it is not uncommon that a laser treatment must be repeated several times and/or excess healthy tissue must be impacted to ensure a successful therapeutic result. This increases the potential for post-therapy complications, can reduce the number of conditions that are treatable, can degrade the accuracy and precision of an intervention, and can lead to an increase in the required operating-room time and cost.

A method for improving the accuracy with which laser-tissue interactions can be predicted would be a significant advance in the state-of-the art.

SUMMARY

Embodiments in accordance with the present disclosure enable improved outcomes for laser therapies, such as laser surgery, tissue ablation, tattoo removal, and the like, by planning a treatment path for a laser signal based on tissue properties inferred from one or more features formed in the treatment site while the laser signal has known optical characteristics.

An illustrative embodiment is an automated laser-surgery system for performing a laser treatment at a treatment site, where the laser treatment includes one or more treatment passes in which a laser signal is used to ablate tissue at the treatment site. During each treatment pass, the laser-surgery system controls a set of parameters of a treatment path based on tissue properties inferred from one or more measurements of a response of tissue at the treatment site to a known laser signal. The controlled parameters of the treatment path include the treatment route through the treatment site for the laser signal, laser-signal parameters (e.g., laser power, spot size, radiant exposure, etc.), the duration of irradiance at each point along the treatment route, the speed at which the laser signal proceeds along the treatment route, and the like. The measured response is obtained by comparing surface scans of the treatment site taken before and after the laser signal is used to generate an interrogation feature at the treatment site. This comparison enables a direct measurement of the shape of the interrogation feature, which indicates the manner in which the tissue responds to a laser signal having known characteristics at each point of the interrogation feature. By modeling these laser-tissue interactions, tissue properties at each point can be inferred. The inferred tissue properties are then used to plan a treatment path for the laser signal during a subsequent treatment pass through the treatment site.

In the illustrative embodiment, the interrogation feature is a test crater formed by ablating tissue while directing the laser signal at a single point and controlling the parameters of the laser signal. In some embodiments, an interrogation feature is generated by performing a treatment pass through the treatment site and the tissue properties are inferred from the induced change in the treatment site to inform the treatment path of the laser signal during one or more subsequent treatment passes. In some embodiments, the interrogation feature is characterized by a tissue change other than tissue removal, such as a color change, cauterization, thermal necrosis, etc.

In some embodiments, a model and/or scan of the treatment site is used to identify multiple tissue types of interest before an interrogation feature is generated, and the laser signal is controlled such that it interacts with each tissue type of interest during the formation of the interrogation feature. As a result, analysis of the of the laser signal feature enables inference of one or more tissue properties for each tissue type of interest.

In some embodiments, the inferred tissue properties are used to locate different tissue types and/or identify boundaries between regions of different tissue types (e.g., a border between tumorous tissue and healthy tissue, etc.). In some embodiments, this is done at the beginning of a surgery to delineate regions that are to be treated (e.g., removed, etc.) from regions of healthy tissue. In some embodiments, it is done multiple times during a complete treatment procedure, for example, when the boundaries between regions of different tissue types change or when the shape/size of the regions is different for different treatment passes (e.g., at different depths in the treatment region).

In some embodiments, an interrogation feature is formed to enable pathological diagnostics, such as to confirm the presence or absence of a particular tissue type (e.g., cancerous tissue, etc.).

An embodiment in accordance with the present disclosure is a laser-treatment system comprising: a laser configured to provide a laser signal to a treatment site; a surface-measurement system that is configured to measure the topography of the treatment site; and a processing circuit that is configured to: (1) control the laser to create a first feature in the treatment site; (2) receive a first surface profile of the treatment site from the surface-measurement system; and (3) estimate a first tissue parameter for a first tissue included in the treatment site, the first tissue parameter being estimated based on a first difference between the first surface profile and a second surface profile of the treatment site, the second surface profile being generated before the creation of the first feature.

Another embodiment in accordance with the present disclosure is a method comprising: controlling a laser signal to create a first feature in the treatment site; generating a first surface profile of the treatment site, wherein the first surface profile is generated after the first feature has been created; and estimating a first tissue parameter for a first tissue included in the treatment site, wherein the first tissue parameter is estimated based on a first difference between the first surface profile and a second surface profile that is generated before the creation of the first feature.

DETAILED DESCRIPTION

Figure 1:
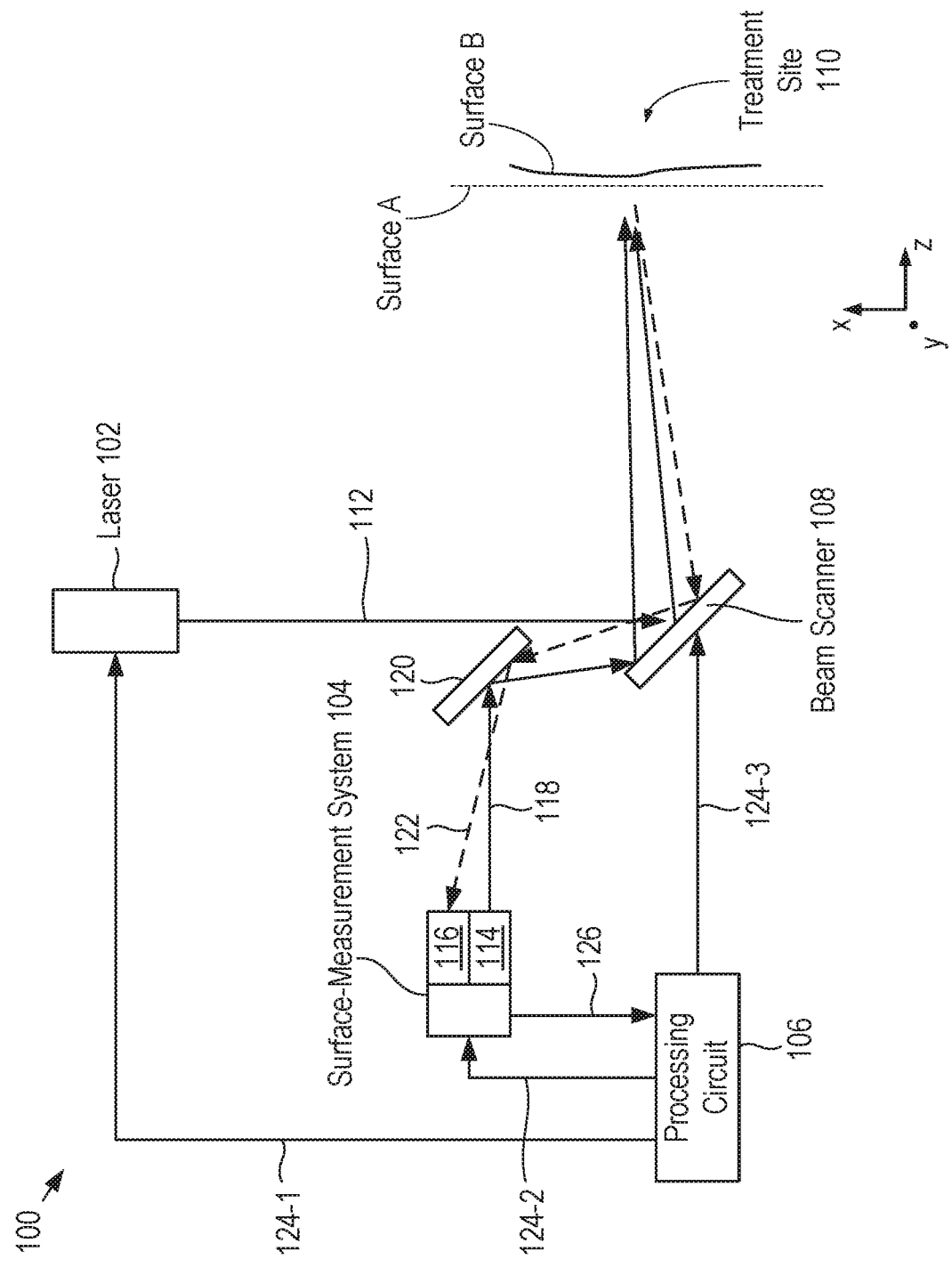
FIG. 1 depicts a schematic drawing of a laser-treatment system in accordance with aspects of the present disclosure.

FIG. 1 depicts a schematic drawing of a laser-treatment system in accordance with aspects of the present disclosure. System 100 includes laser 102, surface-measurement system 104, processing circuit 106, and beam scanner 108.

System 100 is a computer-controlled laser-surgery system operative for treating tissue at treatment site 110. For the purposes of this Specification, including the appended claims, the term "tissue treatment" is defined as interacting with a tissue to effect a desired change, such as ablating tissue material, inducing necrosis in the tissue, inducing a chemical change to an ink or other foreign substance in the tissue, inducing coagulation, cutting, heating, illuminating, disrupting, and the like.

In the depicted example, system 100 is configured to controllably ablate soft brain matter at treatment site 110; however, it should be noted that laser-treatment systems suitable for use in other procedures, such as tattoo removal via laser-induced chemical breakdown of tattoo inks, laser-induced thermal necrosis for treatment of skin-cancer cells, removal of other soft pathological tissues, coagulation or ablation of vascular lesions and vascular structures, removal of both benign and malignant tissues, among others, can be used without departing from the scope of the present disclosure. Examples of laser-treatment systems suitable for use in embodiments in accordance with the present disclosure are described in PCT Application No. PCT/US2018/018838, which is incorporated herein by reference.

Furthermore, although system 100 is a computer-controlled laser-surgery system, other laser-treatment systems, such as hand-held laser-treatment systems, non-computer-controlled laser-treatment systems, robotic-assisted laser-treatment systems, tele-operated laser-treatment systems, and the like, can be used in system 100 without departing from the scope of the present disclosure.

Laser 102 is a conventional carbon-dioxide ($CO_2$) surgical laser, which provides laser signal 112 to beam scanner 108. Laser signal 112 has a wavelength of approximately 10.6 microns and is operative for ablating biological material to perform tissue removal. In some embodiments, laser 102 is a different laser, such as a neodymium-doped yttrium aluminum garnet (Nd:YAG) laser, a Q-switched laser suitable for removal of tattoo ink, a pulsed-dye laser for treating basal cell carcinoma, and the like. The choice of source for laser 102 is based on several factors, such as intended application, the material properties of the tissue to be manipulated, location of the tissue to be manipulated. Myriad lasers can be used in laser 102 without departing from the scope of the present disclosure.

In some embodiments, a visible-light guidance signal is combined with laser signal 112 to provide a user with a visible indication of the position of the laser signal in real time.

Surface-measurement system 104 is a conventional surface profiler configured to acquire surface scans of treatment site 110 and provide topographical information about the site to processing circuit 106 as range signal 126. Typically, the surface scan yields range data (position along the z-direction) for one or more points on the surface of the treatment site. In some embodiments, range signal 126 comprises raw range data and processing circuit 106 generates a surface profile of the treatment area based on the raw data. In some embodiments, range signal 126 comprises a surface profile that is generated based on the acquired range data. In some embodiments, surface-measurement system 104 includes conventional scanning technology (e.g., optical coherence tomography (OCT), digital cameras, etc.) that is also operative for providing information about sub-surface structure of treatment site 110 to processing circuit 106.

In the depicted example, surface-measurement system 104 includes a laser-triangulation sensor that comprises solid-state laser light source 114 and detector array 116 (typically a CMOS/CCD detector array). Light source 114 provides scanning signal 118, which is directed to treatment site 110 via conventional mirror 120 and conventional beam scanner 108. A portion of scanning signal 118 is reflected back from treatment site 110 as reflected signal 122, which is directed to surface-measurement system 104 via beam scanner 108 and mirror 120 and focused onto detector array 116 via suitable focusing optics. The position at which reflected signal 122 strikes the detector array is a function of the range (i.e., z-position) of the point on the surface of treatment site 110 on which scanning signal 118 is incident. As the tissue at this point is ablated by laser signal 112, the range at the point increases and the position of reflected signal 122 on the detector array shifts commensurately.

In the depicted example, scanning signal 118 has a wavelength of approximately 670 nm; however, myriad wavelengths can be used for scanning signal 118.

Processing circuit 106 comprises processing circuitry, control circuitry, memory, and the like, and is configured to, among other things, provide control signals 124-1, 124-2, and 124-3 to laser 102, surface-measurement system 104, and beam scanner 108, respectively, receive range signal 126 from surface-measurement system 104, estimate one or more tissue parameters for one or more tissue types at treatment site 110, identify locations and/or regions of tissue types at treatment site 110, generate a desired treatment path through treatment site 110 for laser signal 112, store one or more pre-generated three-dimensional (3D) maps of treatment site 110, utilize and tune a tissue-manipulation model simulator, and generate an assessment of the success of a surgical procedure based on a comparison of the measurement data received from surface-measurement system 104 and a stored 3D map of the treatment site.

In the embodiment depicted in FIG. 1, the processing circuit is implemented as a single, discrete component within system 100. In various other embodiments, the processing circuit can be distributed, at least in part, among multiple components of system 100, implemented, in part or in full, in a remote or cloud-based computing system, or otherwise implemented in a suitable arrangement for carrying out the functions described herein.

Beam scanner 108 is a conventional two-axis scanning-mirror system for steering laser signal 112 and scanning signal 118 in two dimensions. In the depicted example, beam scanner 108 is a two-axis galvanometer mirror system; however, there are many two-axis beam steering systems suitable for use in beam scanner 108. Beam scanners suitable for use in embodiments in accordance with the present disclosure include, without limitation, two-axis gimbal-mounted mirrors, pairs of single-axis turning mirrors, MEMS beam-steering mirrors, and the like.

In use, the beam scanner is typically positioned in close proximity to the treatment site, while bulky laser sources, processing circuits, computing systems, etc. are located remotely. This mitigates sterilization issues and improves the visibility of the treatment site for the surgeon or other operator.

It should be noted that system 100 typically also includes various optical elements for manipulating and/or shaping light signals, such as collimating optics, focusing optics, spatial and spectral filtering optics, and the like.

Unfortunately, the outcome of a laser treatment can be difficult to predict with certainty. While mathematical models exist that purport to describe the feature geometry that will result from interaction between tissue and a laser signal, tissue parameters can change across tissue types, the state of the tissue, each patient, and even within the same tumor. As a result, it is difficult to correctly plan the treatment path of a laser signal through a treatment site given the state of the prior art.

It is an aspect of the present disclosure, however, that one or more tissue types at a treatment site and/or their tissue properties can be accurately determined in-situ rapidly and intraoperatively by using a laser signal with known characteristics to form an interrogation feature at the treatment site, determining the actual response of the irradiated tissue to the laser signal, and using this measured response to extract the tissue characteristics from a model of the interrogation feature. As a result, more accurate tissue-laser interaction models can be developed, thereby enabling better prediction of the manner in which irradiated tissue will react to a laser signal and enabling the planning of a treatment path for the laser signal through a treatment site. For the purposes of this Specification, including the appended claims, the term "treatment path" is defined as the set of parameters controlled for laser signal 112 during a treatment pass, including the treatment route over which the laser signal is directed (e.g., scanning speed, scanning direction, positional step size, dwell time at each point along the treatment route, etc.), the instantaneous laser settings at each point along the treatment route (e.g. peak optical power, focal length, incident radiant exposure, etc.) and the like.

Figure 2:
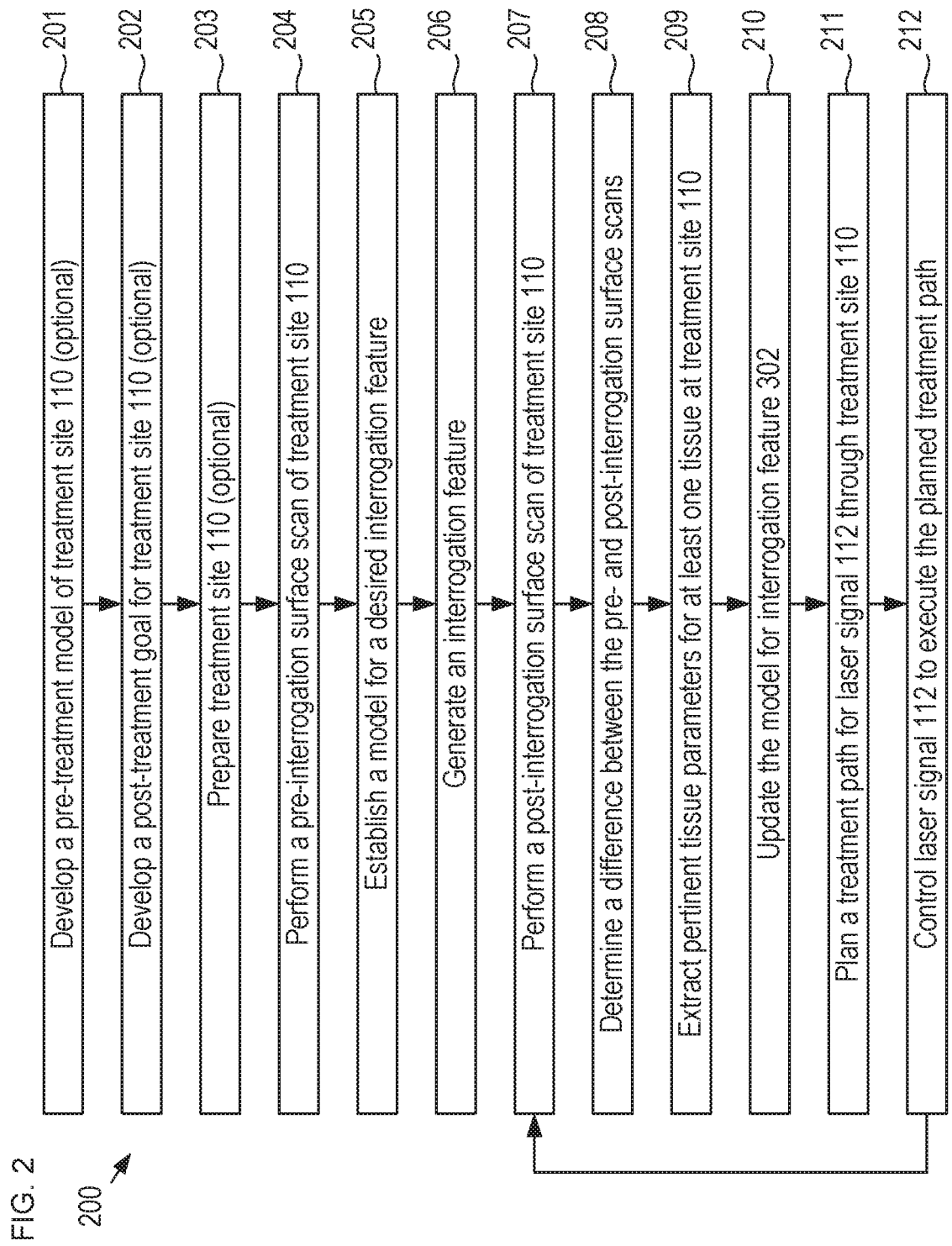
FIG. 2 depicts a method for performing a laser-treatment procedure at a treatment site.

FIG. 2 depicts a method for performing a laser-treatment procedure at a treatment site. Method 200 is described with continuing reference to FIG. 1, as well as reference to FIG. 3A.

Method 200 begins with optional operation 201, wherein a pre-treatment model of treatment site 110 is developed. In the depicted example, the pre-treatment model is a three-dimensional (3D) model based on a magnetic resonance imaging (MRI) image of treatment site 110. In some embodiments, a different imaging modality is used to create a pre-procedural image of the treatment site. Examples of alternative imaging modalities suitable for use in embodiments in accordance with the present disclosure include, without limitation, computed tomography (CT), optical coherence tomography (OCT), x-ray imaging, ultrasound, spectroscopy, microscopy, endoscopy, visible light camera, surface scanning, and the like.

At optional operation 202, a post-treatment goal is developed for treatment site 110. In the depicted example, the post-treatment goal is a three-dimensional model of the desired state of the treatment site after the treatment has been completed.

At operation 203, treatment site 110 is prepared. In the depicted example, site preparation entails enabling access to the treatment site (e.g., by removing a portion of the patient's skull, making an incision, creating an access hole, etc.), removal of incidental tissue from the treatment site (e.g., opening the lining that surrounds the brain, etc.), and the like. It should be noted that, in some embodiments (e.g., dermatological applications, tattoo removal, etc.), nothing needs to be removed to expose the treatment site for interaction with the surgical laser signal.

At operation 204, a first surface scan of treatment site 110 is performed. The first surface scan is a pre-interrogation scan (i.e., it is performed before the formation of an interrogation feature at the treatment site).

In the depicted example, to perform a surface scan of the treatment site, processing circuit 106 provides control signals 124-2 and 124-3 to surface-measurement system 104 and beam scanner 108, respectively. In response, surface-measurement system 104 generates scanning signal 118 and beam scanner 108 sweeps it over a plurality of points on the surface of the treatment site. At each point, light is reflected back as reflected signal 122, which is directed to detector array 116 by beam scanner 108 and mirror 120. The position at which the reflection signal hits the detector array is dependent upon the range (i.e., depth into treatment site 110) of the point from which it reflects.

Surface-measurement system 104 provides range signal 126 to processing circuit 106, where the range signal includes triangular-sensor data for the plurality of points over which scanning signal 118 is scanned.

Processing circuit 106 converts the triangular-sensor data into a range value for each point by correlating each distance sample the angular position of beam scanner 108 when that point was measured. The resultant set of range values forms the surface scan of the treatment site.

It should be noted that the use of a laser-triangulation sensor to perform three-dimensional scanning of the treatment site is preferred, since it is a low-cost imaging method and mitigates impact on the treatment site while still providing a good level of precision; however, other imaging modalities can be used to image treatment site 110 without departing from the scope of the present disclosure. Imaging modalities suitable for use with embodiments described herein include, without limitation, ultrasound, CT, MRI, 3D imaging, 3D surface scanning (e.g., via a non-contact surface-measurement system, surface profiler, etc.), interferometry, conoscopic holography, visible light cameras, computer vision systems, and the like.

At operation 205, a model for a desired interrogation feature is established. A typically photoablation model describes the effects of laser irradiance on a tissue surface, where the model is a function of laser parameters (e.g., laser power, the duration of irradiance, spot size, radian exposure, etc.) and the mechanical and optical properties of the tissue (e.g., tissue density, absorption coefficient, scattering coefficient, ablation enthalpy, radiant threshold, etc.).

In the depicted example, the desired interrogation feature is an ablation crater to be formed in treatment site 110 by directing laser signal 112 such that it is stationary at a single point on the surface of the treatment site, controlling the power of the laser signal such that its peak irradiance remains substantially constant (assuming a Gaussian profile for the laser signal), and irradiating that point for a set time period.

A suitable model for such an ablation crater can be described as:

$$\delta_{fit}(r) = A^* - \frac{dt}{\beta}E_0 e^{-2\left(\frac{r^2}{\omega_0^2}\right)}, \quad (1)$$

where $\beta\rho^*habl$ (p being tissue density and haw being ablation enthalpy), dt is the period of irradiation, $A^*$ is corresponds to a theoretical surface height of the tissue if the tissue radiant threshold were zero, r is the distance from the center of the beam, $E_0$ is the peak irradiance value of the beam, and $\omega_0$ is the $1/e^2$ spot size of the laser signal. This approach is based on the assumptions that the true value of the tissue radiant threshold, $\Phi_{th}$, of treatment site 110, which is not zero, can be derived from parameters fit to Equation (1) of a theoretical tissue with zero radiant threshold and that laser signal 112 is a Gaussian beam.

Equation (1) includes two fitting parameters: $A^*$ and $\beta$. Subsequent calculations based on these fitting parameters enables accurate estimation of tissue parameters pertinent to the model.

It should be noted that, while Equation (1) is one model for an ablation crater, other suitable ablation-crater models are known and can be used in accordance with the present disclosure. Furthermore, in some embodiments, the desired interrogation feature is a feature other than an ablation crater, such as a line, a plurality of lines, a pattern, etc. Still further, in some embodiments, the model is based on a different effect that can be achieved at a treatment site, such as a color change (e.g., for tattoo removal), and the like.

At operation 206, interrogation feature 302 is formed at treatment site 110.

At operation 207, a second surface scan of treatment site 110 is performed as described above and with respect to operation 204. The second surface scan is a post-interrogation scan (i.e., it is performed after the formation of interrogation feature 302).

At operation 208, a difference between the first and second surface scans is determined. This difference indicates the response of at least one tissue included in interrogation feature 302 to laser signal 112.

Figure 3A:
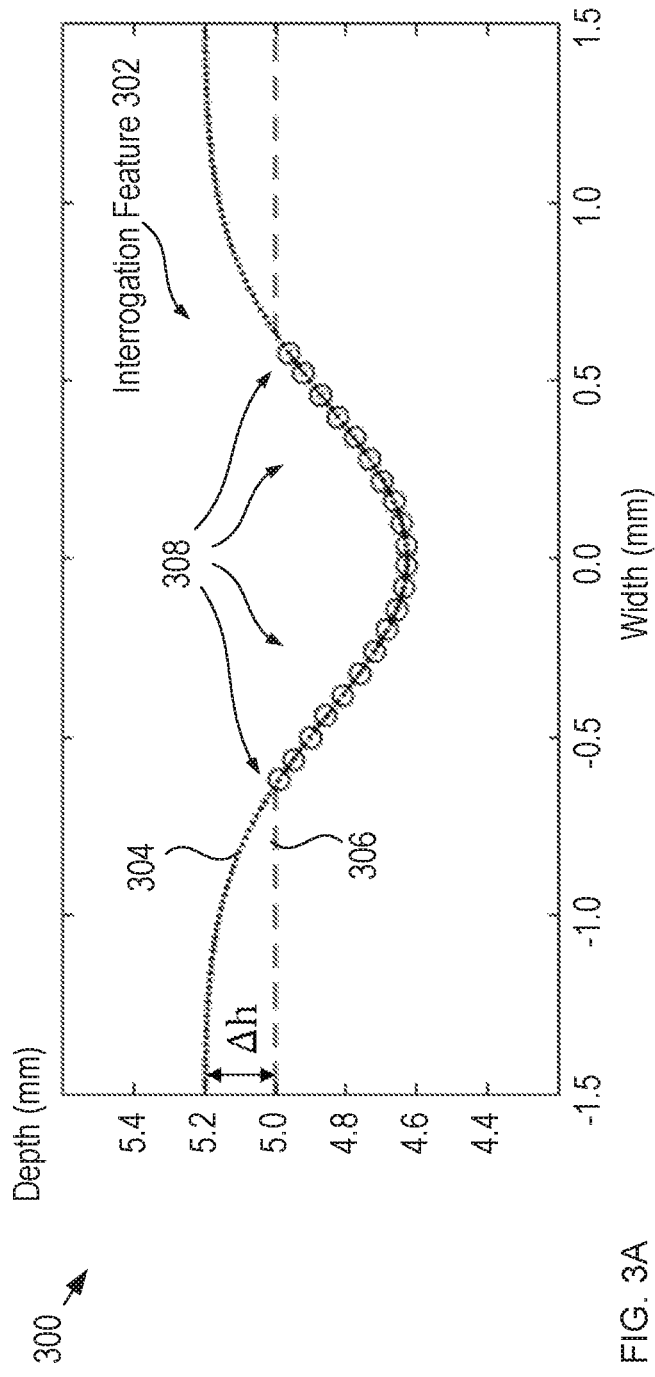
FIG. 3A depicts an example of a representative model fit in accordance with the illustrative embodiment.

FIG. 3A depicts an example of a representative model fit in accordance with the illustrative embodiment. Plot 300 shows the relationship between fitted model 304 and surface scan 306, which is taken after the formation of the desired interrogation feature. Points 308 denote the points used for the fit of the measured data to the model represented by Equation (1).

Tissue response to irradiation with a known laser energy, wavelength, and power profile is a function of many tissue parameters—including, but not limited to, threshold radiant exposure, $\Phi_{th}$, tissue density, $\rho$, ablation enthalpy, $h_{abl}$, absorption coefficient, $\mu_a$, optical scattering coefficient, $\mu_s$, reduced scattering coefficient, $\mu_s'$, refractive index, n, and scattering anisotropy coefficient, g. Furthermore, a descriptive model of laser ablation or, more generally, laser manipulation of tissue, may take into account any of such parameters.

In addition, the shape and depth of interrogation feature 302 is affected by other characteristics of laser signal 112, such as laser power and the length of time that the laser signal interacts with the tissue (i.e., dwell time).

Figure 3B:
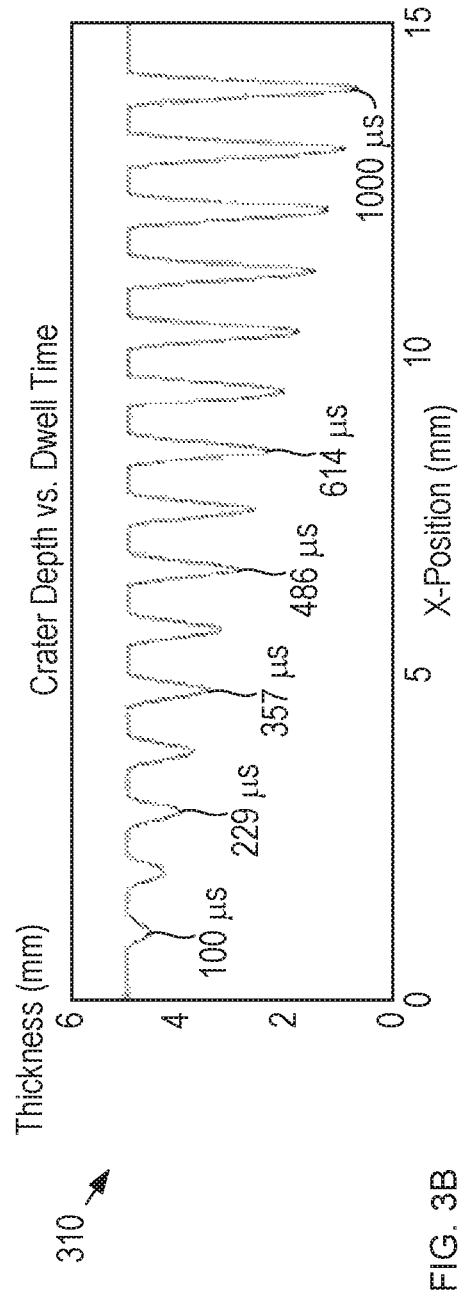
FIG. 3B depicts the relationship between the physical characteristics of a single-point crater and dwell time for an interaction between tissue and a laser signal 112.

FIG. 3B depicts the relationship between the physical characteristics of a single-point crater and dwell time for an interaction between tissue and a laser signal 112.

At operation 209, pertinent tissue parameters are extracted. In the depicted example, the tissue parameters extracted are $\beta$ (i.e., $\rho^*habl$) and the radiant threshold of the treatment site, $\Phi_{th}$.

Values for $\beta$ and $A^*$ are derived via the model fit depicted in plot 300. It should be noted that, to improve the fit of the beam profile to the realized ablation crater without forcing it to fit to the non-smooth edges of the crater, the radiant threshold, $\Phi_0$, is set to zero and the theoretical initial surface height $A^*$ is allowed to float.

Using the derived values of $\beta$ and $A^*$, $\Phi_{th}$ is given by:

$$\Phi_{th} = (A^* - A)\frac{\beta}{dt} \quad (2)$$

where $(A^*-A)=\Delta h$, as depicted in FIG. 3, $A^*$ is the theoretical tissue-surface height from the model fit, and A is the actual initial tissue-surface height determined during the first surface scan of treatment site 110 performed in operation 204.

At operation 210, using the extracted values for $\beta$ and $\Phi_{th}$, the model of the formed interrogation feature is updated to more accurately represent the tissue properties the tissues contained in treatment site 110.

At operation 211, a desired treatment path for laser signal 112 through treatment site 110 is planned based upon the extracted tissue properties and the updated model. In the depicted example, the parameters established as part of the planned treatment path include laser-signal characteristics (e.g., peak power, focal length, beam diameter, incident radiant exposure, etc.), treatment route characteristics (e.g., scanning speed and direction, raster step size, etc.), and dwell time at each point along the treatment route.

At operation 212, laser signal 112 is controlled to execute the planned treatment path.

After operation 212, an assessment is typically made by a surgeon or other user as to whether one or more additional treatment passes are necessary to realize the post-treatment goal. If additional treatment is desirable, method 200 returns to operation 207, where another surface scan of treatment site 110 is performed. In such cases, the result of the most recent treatment pass serves as a new interrogation feature, where a mathematical model for the realized feature geometry is used for the extraction of tissue parameters in operation 209. Typically, the quality of the extracted tissue parameters increases with each iteration of operations 207 through 212.

As noted above, interrogation feature 302 can have a shape other than a "single-point" crater without departing from the scope of the present disclosure. Interrogation features in accordance with the present disclosure include, without limitation, continuous features, discontinuous features, circular features, linear features, a plurality of features (at a single depth or at multiple depths), amorphous-shaped features, uniform patterns, non-uniform patterns, etc. In some embodiments, the shape of an interrogation features is based on a priori knowledge of one or more tissue types within treatment site 110. In some embodiments, one treatment pass through treatment site 110 serves as an interrogation feature that informs a second treatment pass through the treatment site.

Although method 200 is described herein with emphasis on a computer-controlled laser system, it should be noted that embodiments in accordance with the present disclosure are also applicable to hand-held laser systems, such as smart-laser systems, etc. In some such embodiments, after the pertinent tissue parameters are extracted and the model of the interrogation feature is updated, a user inputs features of a desired feature (e.g., a hole, line, etc.), such as depth, width, and/or shape into the smart-laser system, which would then establish the laser-signal parameters (e.g., power, pulse width, focus, etc.) suitable for realizing the desired feature. The user would then direct the laser signal to a desired location and form the desired feature.

For example, a hole at a desired location could be created by inputting the desired hole depth/width to a smart-laser system and directing the laser signal to the location at which the hole is desired. The smart-laser system would then create the hole on a laser-burst-by-laser-burst basis, where, between each laser burst, a surface scan of the location is performed, the tissue parameters and model are updated, and the laser-signal parameters are refined based on the updated model in preparation for the next laser burst. In some cases, the first laser burst in the sequence generates the interrogation feature as in operation 206.

Figure 4:
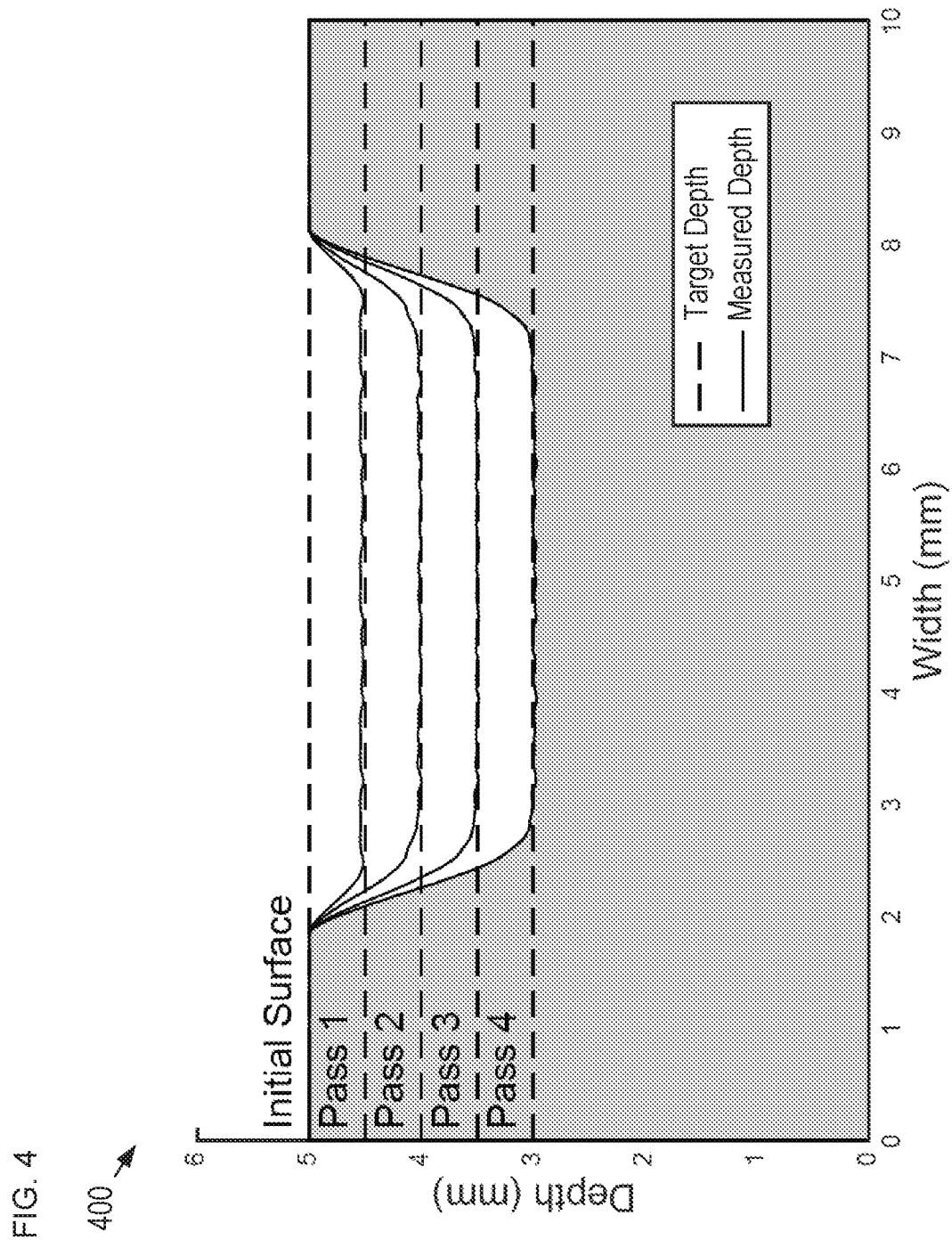
FIG. 4 depicts a cross section of an exemplary series of treatment passes through treatment site 110.

FIG. 4 depicts a cross section of an exemplary series of treatment passes through treatment site 110. Plot 400 shows the results of four successive treatment passes through the treatment site, and where each treatment pass is an ablation cut whose depth is increased by approximately 0.5 mm. Plot 400 illustrates that with each iterative pass, tissue is removed. The specific treatment pattern and dimensions shown in FIG. 4 are merely exemplary and any practical treatment region, treatment route, pattern, and cutting dimensions can be used.

For each pass within the series of treatment passes depicted in FIG. 4, laser signal 112 is set to an output continuous wave at a power of 11 W±8% and a $1/e^2$ spot size of approximately 1.75 mm at the treatment site (located approximately six inches from the center of beam scanner 108). Continuous velocity control of laser signal 112 is achieved by providing discrete position commands that are closely spaced (0.5 micron) relative to the spot size of the laser signal. In the depicted example, the position commands are updated at a rate of 20 kHz. In addition, the parameters used for each successive cut are tailored based on extracted tissue parameters whose extraction is improved by additional model refinements based on the depth change achieved during the prior treatment pass. As a result, plot 400 demonstrates that the agreement between the target depth and measured depth for pass 4 is significantly improved over that for pass 1.

Figure 5:
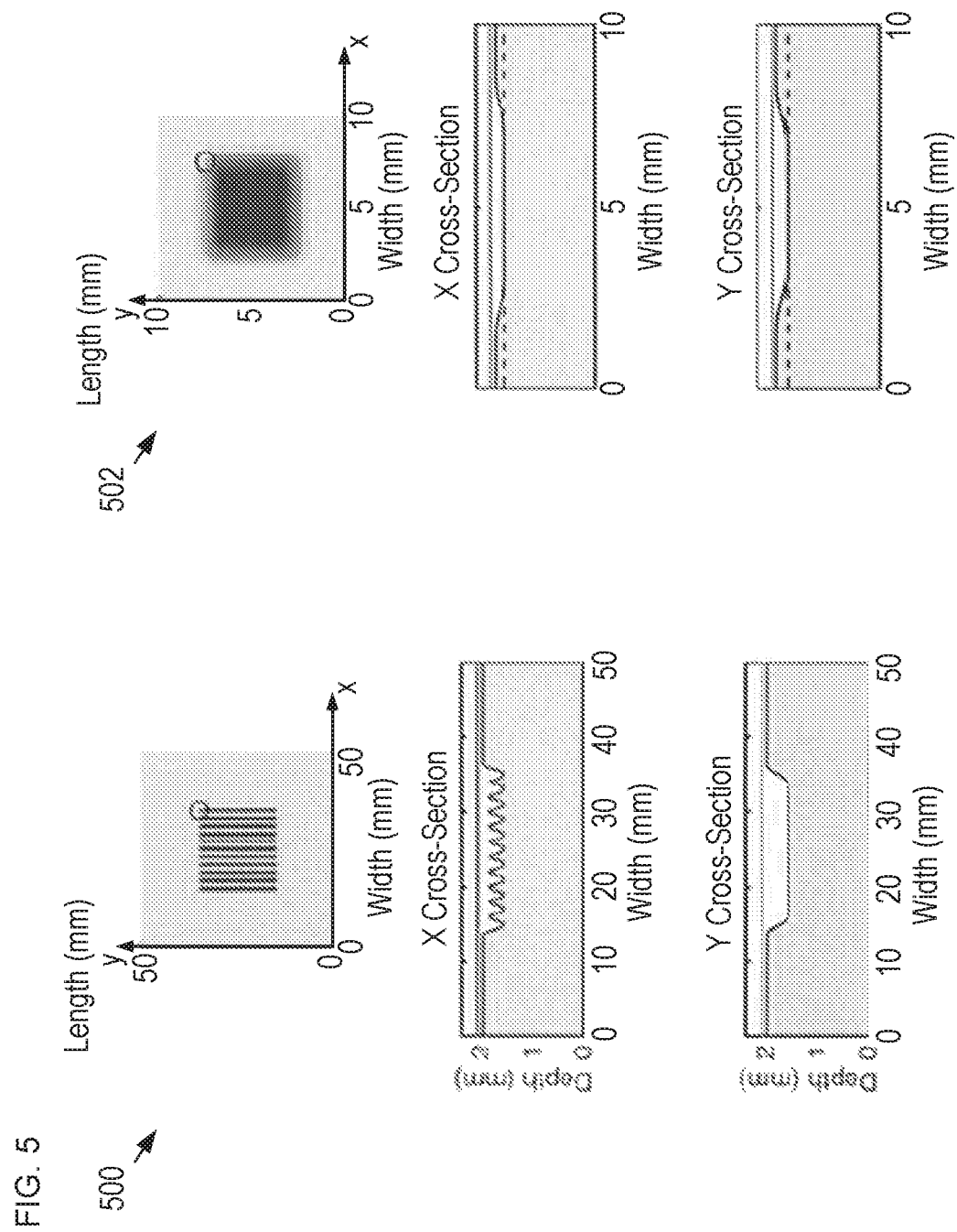
FIG. 5 demonstrates the improvement in a volumetric tissue removal enabled by the teachings of the present disclosure.

FIG. 5 demonstrates the improvement in a volumetric tissue removal enabled by the teachings of the present disclosure.

Plot 500 shows the results of a tissue removal procedure performed by sequentially scanning laser signal 112 along a series of parallel treatment routes to realize a "volumetric" cut without informing the parallel treatment routes of the treatment in accordance with method 200. As evinced by the cross-section taken along the x-direction, the uninformed nature of the parallel treatment routes can lead to significant ridges of residual tissue after the procedure. More generally stated, the desired outcome may not be achieved without the use of method 200.

Plot 502 shows the results of a tissue removal procedure performed in accordance with the teachings of the present disclosure, wherein tissue removal is performed in analogous fashion to that shown in plot 500; however, the parallel paths are planned and executed in accordance with method 200. By virtue of the fact that the tissue response to laser signal 112 is more easily anticipated, the treatment routes through treatment site 110 are planned such that little or no residual tissue remains between the parallel treatment routes taken by the laser signal, and the desired cut is achieved.

It should be noted that, while the volumetric cut depicted in each of plots 500 and 502 are performed via a linear raster pattern of the laser signal, any suitable treatment route for laser signal 112 can be used without departing from the scope of the present disclosure. Suitable treatment routes include, without limitation, continuous treatment routes, discontinuous treatment routes, circular treatment routes, amorphous-shaped treatment routes, etc. In fact, in some embodiments, the identification of one or more tissue types within treatment site 110 dictates the treatment route over which laser signal 112 is directed.

In some embodiments, operations in accordance with the present disclosure enable identification of the location of at least one boundary between tissue types, such as a boundary between a tumor and healthy tissue that abuts or surrounds it. In some cases, identification of one or such boundaries is performed at the beginning of a treatment and can replace optional operation 201. In some cases, it is performed multiple times during a treatment when a boundary is not known or when the boundary might change through the depth of a treatment site.

Figure 6:
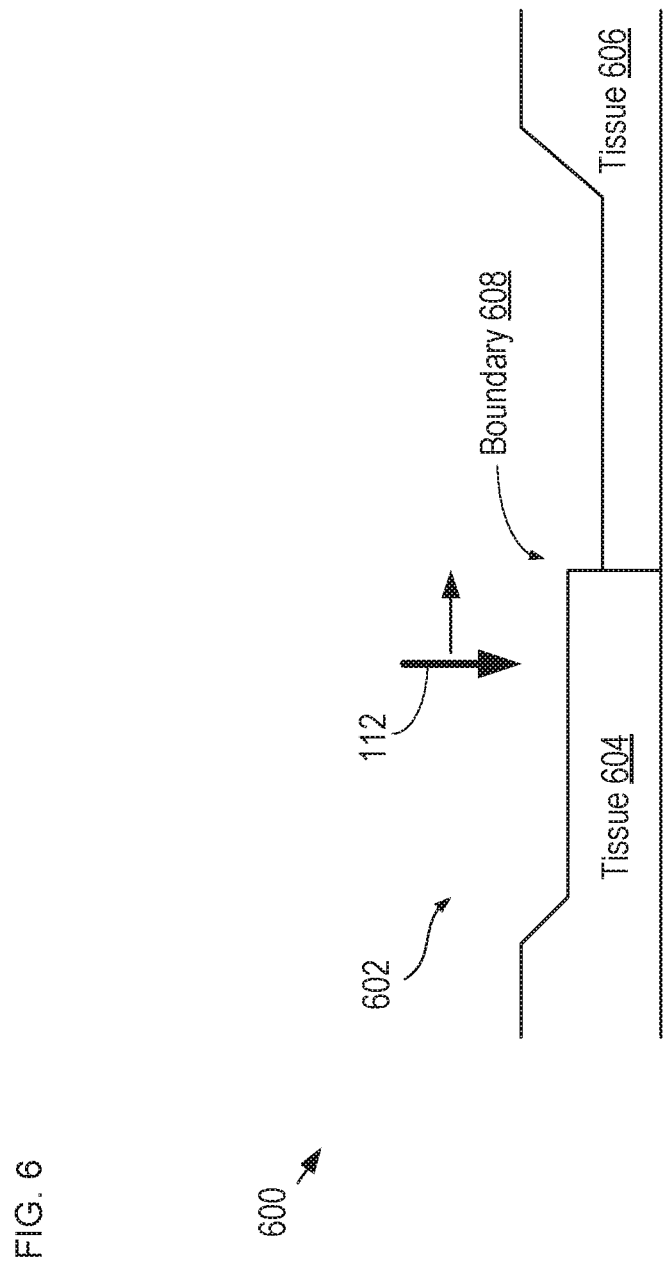
FIG. 6 depicts a schematic drawing of a portion of a treatment site in which an interrogation feature is formed to identify the location of a boundary between two tissue types in accordance with the present disclosure.

FIG. 6 depicts a schematic drawing of a portion of a treatment site in which an interrogation feature is formed to identify the location of a boundary between two tissue types in accordance with the present disclosure. Region 600 is a portion of treatment site 110 in which interrogation feature 602 is formed.

Interrogation feature 602 is analogous to interrogation region 302 described above; however, interrogation feature 602 includes two tissue types that react markedly different to laser signal 112.

In the depicted example, tissue 604 is cancerous tissue and tissue 606 is healthy tissue. Tissues 604 and 606 meet at boundary 608.

As indicated in FIG. 6, tissue 604 ablates differently than tissue 606 when exposed to laser signal 112. In some cases, the differences between the ablation characteristics of different tissue types can give rise to different vertical ablation rates, different lateral ablation rates, and the like, which manifests as, for example, different feature depths, different feature widths, different ablation profiles, etc.

As a result, a surface scan of interrogation feature 602 will exhibit a sharp change at boundary 608, thereby enabling identification of its location within treatment site 110. In some embodiments, formation of interrogation feature 602 is performed in conjunction with the development of a model of treatment site 110 so that the interrogation feature can be positioned in a manner that provides as much information as possible about multiple tissue types of interest within the treatment site.

It should be noted that embodiments in accordance with the present disclosure can be used in conjunction with handheld or computer-guided laser-treatment tools to:
  i. optimize cuts to a particular cutting depth; or
  ii. interrogate a treatment site to map one or more tissue boundaries; or
  iii. improve pathological diagnostics by, for example, determining ablation properties that function as indicators regarding the "tumorous" or "non-tumorous" nature of tissue; or
  iv. plan treatment paths for delivery of laser signal 112 to desired tissue regions (e.g. for superficial laser-ablation, such as tattoo removal, mole excisions, tumor resections, etc., or non-removal/cutting treatment of tissue); or
  v. any combination of i, ii, iii, and iv.

Although the figures show a specific order of method steps, the order of the steps can differ from what is depicted. Also two or more steps can be performed concurrently or with partial concurrence. Such variation will depend on the software and hardware systems chosen and on designer choice, as well as the a priori information about the targeted tissue. All such variations are within the scope of the disclosure. Likewise, software implementations could be accomplished with standard programming techniques with rule based logic and other logic to accomplish the various connection steps, calculation steps, processing steps, comparison steps, and decision steps.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

As used herein, the term "circuit" can include hardware structured to execute the functions described herein. In some embodiments, each respective "circuit" can include machine-readable media for configuring the hardware to execute the functions described herein. The circuit can be embodied as one or more circuitry components including, but not limited to, processing circuitry, network interfaces, peripheral devices, input devices, output devices, sensors, etc. In some embodiments, a circuit can take the form of one or more analog circuits, electronic circuits (e.g., integrated circuits (IC), discrete circuits, system on a chip (SOCs) circuits, etc.), telecommunication circuits, hybrid circuits, and any other type of "circuit." In this regard, the "circuit" can include any type of component for accomplishing or facilitating achievement of the operations described herein. For example, a circuit as described herein can include one or more transistors, logic gates (e.g., NAND, AND, NOR, OR, XOR, NOT, XNOR, etc.), resistors, multiplexers, registers, capacitors, inductors, diodes, wiring, and so on).

The "circuit" can also include one or more processors communicably coupled to one or more memory or memory devices. In this regard, the one or more processors can execute instructions stored in the memory or can execute instructions otherwise accessible to the one or more processors. In some embodiments, the one or more processors can be embodied in various ways. The one or more processors can be constructed in a manner sufficient to perform at least the operations described herein. In some embodiments, the one or more processors can be shared by multiple circuits (e.g., circuit A and circuit B can comprise or otherwise share the same processor which, in some example embodiments, can execute instructions stored, or otherwise accessed, via different areas of memory). Alternatively or additionally, the one or more processors can be structured to perform or otherwise execute certain operations independent of one or more co-processors. In other example embodiments, two or more processors can be coupled via a bus to enable independent, parallel, pipelined, or multi-threaded instruction execution. Each processor can be implemented as one or more general-purpose processors, application specific integrated circuits (ASICs), field programmable gate arrays (FPGAs), digital signal processors (DSPs), or other suitable electronic data processing components structured to execute instructions provided by memory. The one or more processors can take the form of a single core processor, multi-core processor (e.g., a dual core processor, triple core processor, quad core processor, etc.), microprocessor, etc. In some embodiments, the one or more processors can be external to the apparatus, for example the one or more processors can be a remote processor (e.g., a cloud based processor). Alternatively or additionally, the one or more processors can be internal and/or local to the apparatus. In this regard, a given circuit or components thereof can be disposed locally (e.g., as part of a local server, a local computing system, etc.) or remotely (e.g., as part of a remote server such as a cloud based server). To that end, a "circuit" as described herein can include components that are distributed across one or more locations. The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

What is claimed is:

1. A laser-treatment system comprising:
a laser configured to provide a laser signal to a treatment site;
a surface-measurement system that is configured to perform one or more surface scans of the treatment site; and
a processing circuit that is configured to:
(1) control the laser to create a first feature in the treatment site;
(2) develop a model of the reaction of the first tissue to the laser signal based on a first difference between a first topological map of the treatment site and a second topological map of the treatment site, wherein the first topological map is based on a first surface scan of the treatment site performed before the creation of the first feature and the second topological map is based on a second surface scan of the treatment site performed after the creation of the first feature;
(3) estimate a first tissue parameter for a first tissue included in the treatment site based on the model; and
(4) establish at least one laser-signal parameter of the laser signal for a first treatment path through the treatment site based on the estimated first tissue parameter, wherein the at least one laser-signal parameter is selected from the group consisting of peak power, focal length, beam diameter, and incident radiant exposure.

2. The system of claim 1 wherein the processing circuit is further configured to:
(5) plan the first treatment path through the treatment site for the laser signal based on the first tissue parameter; and
(6) control the laser to direct the laser signal along the first treatment path.

3. The system of claim 2 wherein the first treatment path includes a treatment route for the laser signal.

4. The system of claim 2 wherein the processing circuit is further configured to (7) control the at least one laser-signal parameter as the laser signal is directed along the first treatment path.

5. The system of claim 1 wherein the processing circuit is further configured to:
(5) estimate a second tissue parameter for a second tissue included in the treatment site, the second tissue parameter being estimated based on the model, wherein the model is further based on a second difference between the first topological map and the second topological map;
(6) plan the first treatment path based further on the second tissue parameter; and
(7) change the at least one laser-signal parameter based on a difference between the first tissue parameter and the second tissue parameter.

6. The system of claim 5 wherein the processing circuit is further configured to:
(8) identify a first location that includes the first tissue;
(9) identify a second location that includes the second tissue; and
(10) plan the first treatment path based further on the first location and the second location.

7. The system of claim 5 wherein the processing circuit is further configured to:
(8) receive a first model of the treatment site, wherein the first model includes identification of a first location that includes the first tissue and a second location that includes the second tissue; and
(9) control the laser such that the first feature includes the first location and the second location.

8. The system of claim 1 wherein the processing circuit is further configured to:
(5) create a second feature in the treatment site by controlling the laser signal along the first treatment path;
(6) revise the first tissue parameter based on the first difference and a second difference between a third topological map and the second topological map, the third topological map being based on a third surface scan of the treatment site performed after the creation of the second feature; and
(7) plan a second treatment path through the treatment site for the laser signal based on the revised first tissue parameter.

9. The system of claim 1 wherein the processing circuit is further configured to (5) control the laser to create the first feature by scanning the laser signal along a second treatment path through the treatment site.

10. A method comprising:
generating a first topological map of a treatment site based on a first surface scan of the treatment site;
controlling a laser signal to create a first feature in the treatment site after the generation of the first topological map;
generating a second topological map of the treatment site, the second topological map being based on a second surface scan of the treatment site performed after creation of the first feature;
developing a model of the reaction of a first tissue in the treatment site to the laser signal based on a first difference between the first and second topological maps;
estimating a first tissue parameter for the first tissue based on the model, wherein the first tissue parameter is selected from the group consisting of threshold radiant exposure, tissue density, ablation enthalpy, absorption coefficient, optical scattering coefficient, reduced scattering coefficient, refractive index, scattering anisotropy coefficient, and color; and
establishing at least one laser-signal parameter of the laser signal for a first treatment path through the treatment site based on the estimated first tissue parameter, wherein the at least one laser-signal parameter is selected from the group consisting of peak power, focal length, beam diameter, and incident radiant exposure.

11. The method of claim 10 further comprising:
planning the first treatment path through the treatment site for the laser signal based on the first tissue parameter; and
controlling the laser to scan the laser signal along the first treatment path.

12. The method of claim 11 wherein planning the first treatment path includes planning a treatment route for the laser signal.

13. The method of claim 11 further comprising controlling the at least one laser-signal parameter while the laser signal is scanned along the first treatment path.

14. The method of claim 10 further comprising estimating a second tissue parameter for a second tissue included in the treatment site, wherein the second tissue parameter is estimated based on the model, and wherein the model is further based on a second difference between the first topolooical mai, and the second topolooical map, and wherein the first treatment path is planned based on the first and second tissue parameters.

15. The method of claim 14 wherein the laser signal is controlled to create the first feature such that it includes the first tissue and the second tissue.

16. The method of claim 14 further comprising:
identifying a first location that includes the first tissue;
identifying a second location that includes the second tissue; and
planning the first treatment path based further on the first location and the second location, wherein the at least one laser-signal parameter is established differently at the first and the second locations.

17. The method of claim 14 further comprising:
identifying a first region of first tissue;
identifying a second region of second tissue, wherein the second region abuts the first region;
identifying a boundary between the first region and the second region; and
planning the first treatment path based further on the boundary.

18. The method of claim 14 wherein the model includes identification of a first location that includes the first tissue and a second location that includes the second tissue, and wherein the laser signal is controlled such that the first feature includes the first location and the second location.

19. The method of claim 10 further comprising:
creating a second feature in the treatment site by controlling the laser signal along the first treatment path;
revising the first tissue parameter based on the model, wherein the model is further based on the first difference and a second difference between a third topological map and the second, wherein the third topological map is based on a third surface scan of the treatment site performed after the creation of the second feature; and
planning a second treatment path through the treatment site for the laser signal based on the revised first tissue parameter.

20. The method of claim 10 wherein the first feature is created by controlling the laser to scan the laser signal along a second treatment path through the treatment site.

* * * * *